United States Patent [19]

Juge et al.

[11] Patent Number: 4,952,728
[45] Date of Patent: Aug. 28, 1990

[54] PROCESS FOR PREPARATION OF DERIVATIVES OF PHOSPHINOUS ACID AND INTERMEDIATE PRODUCT USED TO THAT EFFECT

[75] Inventors: Sylvain Juge, Orsay; Jean-Pierre Genet, Fontenay-Aux-Roses, both of France

[73] Assignee: Societe Nationale Elf Aquitaine, France

[21] Appl. No.: 89,592

[22] Filed: Aug. 26, 1987

[30] Foreign Application Priority Data

Aug. 27, 1986 [FR]  France ................................ 86 12115

[51] Int. Cl.[5] ................................................ C07F 9/02
[52] U.S. Cl. ........................................ 564/12; 564/13; 556/13; 556/15; 556/19; 556/20; 558/177
[58] Field of Search ...................... 564/12, 13; 556/13, 556/15, 20, 19; 558/177

[56] References Cited

FOREIGN PATENT DOCUMENTS 0082057  6/1983  European Pat. Off. .
3512781 10/1985  Fed. Rep. of Germany .
3518850 11/1985  Fed. Rep. of Germany .
2603286  3/1988  France .

OTHER PUBLICATIONS

Person et al., "Quantitative Prediction and Interpretation of Vibrational Spectra of Organophosphorus Compounds, Part I, Phosphine Oxide (H3PO) and Phosphinous Acid (H2POH)", J. Mol. Struct., 157(1-3), pp. 237-254 (1987), Chem. Abstract No. CA106(26):223290c.

Tsvetkov et al., "A Simple Synthesis and Some Synthetic Applications of Substituted Phosphide and Phosphinite Anions", Synthesis, (3), pp. 198-208 (1986), Chem. Abstract No. CA106(3):18696y.

Primary Examiner—Mark L. Bell
Assistant Examiner—Anthony J. Green
Attorney, Agent, or Firm—Ostrolenk, Faber, Gerb & Soffen

[57] ABSTRACT

New chemical product, constituted by an organic phosphorus compound of the structure

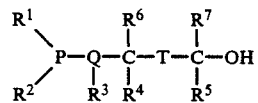

where Q is an N or O atom, T is an alkylene or arylene, possibly carrying substituents, or not existing, while $R^1$ to $R^7$, the same or different, are H or aliphatic, cycloaliphatic and/or arylic hydrocarbon radicals, possibly substituted, $R^3$ not existing when Q is oxygen.

This product is used as an intermediate in the preparation of different derivatives of phosphinous acid.

12 Claims, No Drawings

PROCESS FOR PREPARATION OF DERIVATIVES OF PHOSPHINOUS ACID AND INTERMEDIATE PRODUCT USED TO THAT EFFECT

The invention relates to a process for preparation of derivatives of phosphinous acid. It opens a new way of easy access to phosphinites, phosphines, phosphine oxides, diphosphinites, diphosphines, phosphine dioxides and similar products, by reactions known in themselves, starting from new intermediates according to the present invention. The latter also comprises a process for obtaining these intermediate compounds.

The various compounds named above, derivatives of phosphinous acid, have diverse industrial applications: they serve in the synthesis of various organic phosphorus compounds and are used in the preparation of optically active catalysts comprising optically active organophosphorus ligands. Some phosphines find advantageous application in catalytic systems, for example for the production of mercaptans starting from olefins and $H_2S$. Phosphines are also employed in the preparation of catalysts based on metals: notably for the polymerisation of olefins with the aid of Ni complexes with phosphines, or isomerisation of unsaturated hydrocarbons with complexes of compounds of Ru and phosphines.

Being given the interest which different derivatives of phosphinous acid thus present, it was important to research economic means for their synthesis, in particular their asymmetric synthesis. The present invention responds to this need; it allows the derivatives in question to be obtained in a smaller number of operations than were involved in prior processes. It is possible, thanks to the invention, to obtain optically active compounds, whilst recovering the asymmetric inductor intact.

The intermediate compounds, as well as the derivatives of phosphinous acid, can be in the form of complexes, which generally provide the advantage of an improved stability and lower susceptibility to oxidation.

The intermediate compounds, according to the invention are organic compounds of phosphorus characterised by the structure:

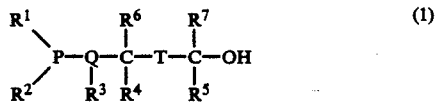

where Q is an N or 0 atom, T is an alkylene or arylene, possibly carrying substituents, or not existing, while $R^1$ to $R^7$, the same or different, are H or aliphatic, cycloaliphatic and/or arylic hydrocarbon radicals, $R^3$ not existing when Q is oxygen. More particularly, the $R^1$ to $R^7$ can be $C_1$ to $C_{18}$ alkyls or alkenyls, especially $C_1$ to $C_6$, or phenyls possibly carrying one or more $C_1$ to $C_6$ alkyl substituents. This signifies that certain of the $R^1$ to $R^7$ groups can be aryls, and others alkyls, cycloalkyls or alkenyls, possibly substituted.

In particular $R^1$ can be methyl, ethyl, propyl or butyl, $R^2$ being phenyl, or vice-versa.

These compounds can exist and be used in the form of complexes with the phosphorus atom bonded to a metal compound M:

The metal complexants can be, for example, different carbonyls of transition metals, in particular $W(CO)_5$ or $Mo(CO)_5$, metal halogens such as CuBr, hydrides, notably $BH_3$, etc.

Moreover, the invention comprises the di-compounds of the formula (1), which can be represented by the formula (2) below:

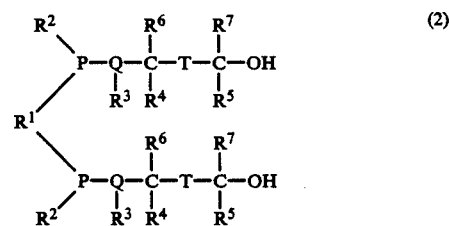

where $R^1$ is a divalent hydrocarbon radical, particularly an alkylene, cycloalkylene or arylene.

As in the case of the mono-compounds, the dicompounds of the formula (2) can be complexed on one or both of the P atoms.

When Q is a nitrogen atom, the intermediate compounds according to the invention are hydroxy monoaminophosphines and dihydroxy di-(amino phosphines)

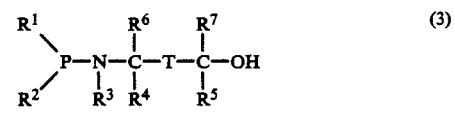

and

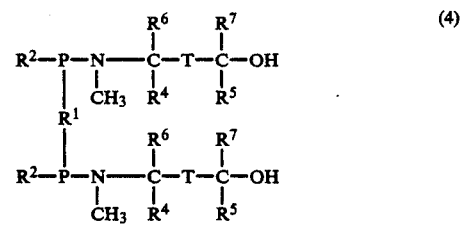

When Q is an oxygen atom, these compounds are respectively phosphinites and diphosphinites of the hydrocarbon radical $-CR^4R^6-T-CR^5R^7-OH$, which carries an hydroxyl at the end of the chain.

Some of these intermediate compounds are described, by way of examples, below, after the description of a process for their preparation.

The intermediate products, according to the invention are prepared by a process characterised in that an organometallic compound is reacted with an oxazaphosphacycycloalkane, a di-oxazaphosphacycloalkane, a dioxaphosphacycloalkane or a bis-dioxaphosphacycloalkane, and the organometallic salt formed is then hydrolysed.

Put otherwise, a preparation according to the following scheme is carried out:

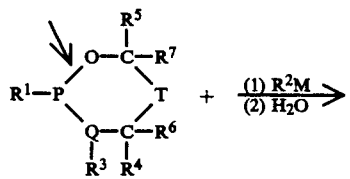   (5)

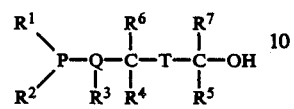

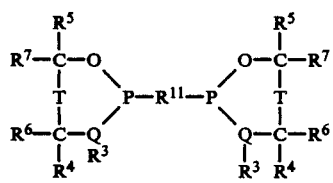   10 or, in analogous fashion, starting from a di-compound:

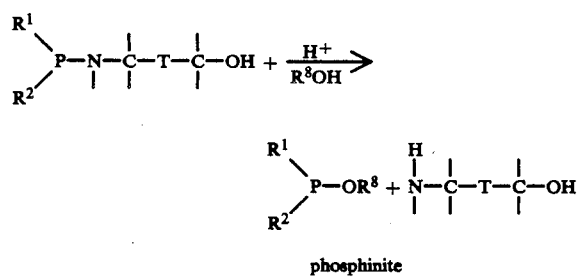   (6)

Common organometallic compounds, such as compounds of magnesium, aluminium, zinc etc. and, most particularly, organolithium compounds, notably aryl lithium compounds and alkyl lithium compounds with $C_1$ to $C_{12}$ alkyls are suitable for the carrying out of the invention. $R^{11}$ is alkylene or arylene.

The reaction can take place with an oxa-compound as starting material complexed on the phosphorus, to give intermediate complexes, as indicated above, with reference to compound (1).

Beginning with intermediates (1) and (2), it is easy to go economically to different phosphinous acid derivatives, of industrial interest, in general by reactions known in themselves.

Thus one can, starting with a hydroxylated aminophosphine (3), reach a phosphinite by alcoholysis:

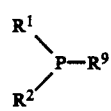

phosphinite and the phosphinite can be converted to phosphine $$R^1\!\!\diagdown\!\!P\!-\!R^9 \atop R^2\!\diagup$$

by the action of an $R^9$ aryl or alkyl organometallic compound, in particular of Mg or Li. This allows optically active trialkyl-, dialkyl-, aryl-, aryldialkyl- and triaryl- phosphines to be obtained with good yields.

Another application of the intermediate product (3) is in the synthesis of a phosphine oxide, by the action of an alkyl halide on the aminophosphine (3):

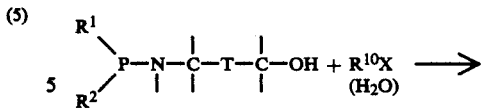

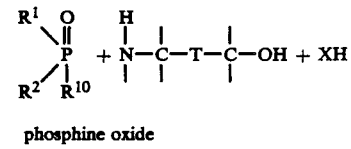

phosphine oxide

One such reaction took place with good yield and allowed the phosphine oxide with an optical purity of 40–100% to be obtained.

Also, a halogenophosphine

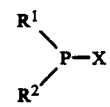

can be obtained by the action of a hydrohalic acid HX on the compound (3). The phosphinous acid itself can be produced by hydrolysis of the compound (3).

Such compounds, except the phosphine oxide, can be obtained in the complexed form, by the same reactions applied to a complex

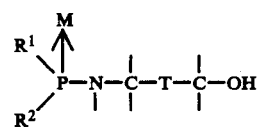   (3')

where M represents a complexing metal group, in particular $W(CO)_5$, $Mo(CO)_5$ or $BH_3$.

In analogous manner one can obtain a diphosphinite, a phosphine dioxide, a dihalogenophosphine or a phosphinous diacid by, respectively, the alcoholysis, action of an alkyl halide, action of a hydrohalic acid, or hydrolysis of a di-hydroxyaminophosphine (4) mentioned above.

As shown in relation to reaction (5), an intermediate product according to the invention can be prepared by the action of an organometallic compound and hydrolysis on a cyclic phosphorus compound of which the ring comprises (as Q) a nitrogen or oxygen atom. When Q is O, the cyclic starting material compound (5) is a dioxaphosphacycloalkane

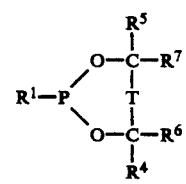

which, after reaction with an organometallic compound $R^2M$ and subsequent hydrolysis, gives a phosphinite

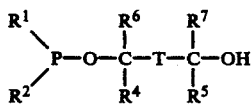

(7)

In the same manner a bis-dioxaphosphacycloalkane according to formula (6) gives a diphosphinite analagous to compound (2).

This manner of preparation of intermediate compounds, according to the invention, is particularly practical and economical, since the starting material, that it is to say the dioxaphosphacycloalkanes and the bis-dioxaphosphacycloalkanes, are easily obtained, particularly by condensation of commercial dichlorophosphine with a corresponding diol. They lead regio- and stereospecifically to phosphinites (7).

As aminophosphines (3), the hydroxylphosphinites (7) permit synthesis of various derivatives of phosphinous acid, in particular asymmetric synthesis thereof. Thus, phosphine oxides are produced by reaction with alkyl halides; phosphines by the action of an organometallic compound, possibly complexed, for example CuBr, W(CO)$_5$ or BH$_3$.

It is noted that, after having used a commercial symmetric phosphine, such as a dichlorophosphine, for the preparation of the dioxaphosphacycloalkane starting material, one can obtain stereo-selectively, according to reaction (5) and a second treatment with an organometallic compound, a new asymmetric phosphine. To do so, the following is carried out after the first operation (5):

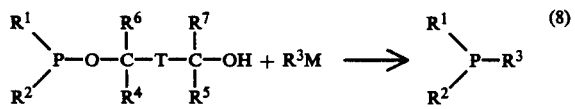

(8)

It is also to be observed that, within the framework of the invention, it possible to use asymmetric inductors, easily accessible at little cost, such as chloramphenicol, the derivatives of ethyl lactate or the camphoquinone.

On the other hand, as will be seen, a phosphine can be prepared in only three steps starting from a diol, the latter two steps, that is to say the reactions (5) and (8) being capable of being carried out in the same solvent medium, the one after the other. Besides, the phosphine can be complexed in that same medium, to give a stable, easily stored compound.

All the reactions which produce phosphinites (7) can also be carried out in analagous manner with diphosphinites

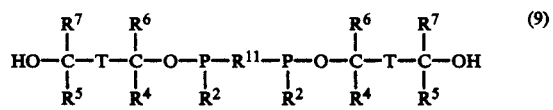

(9)

The invention is illustrated by the non-limiting examples which follow:

EXAMPLE 1

Preparation of N-methyl N-(1-hydroxy 1-phenyl 2-propyl) methyl phenyl aminophosphine (Sp, 1R, 2S)

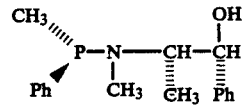

(10)

that is to say the compound of formula (3), given above, in which R$^1$ and R$^4$ are methyls and R$^2$ and R$^5$ phenyls, R$^6$ and R$^7$ being hydrogen atoms, whilst T is only a simple bond.

The preparation is carried out according to reaction (5) in the following manner.

In a 100 ml flask, fitted with a stirrer, 1 mmole (271 mg) of oxazaphospholidine

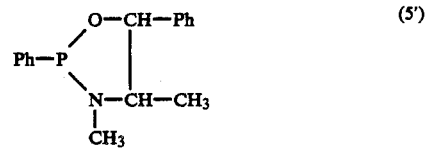

(5')

$[\alpha]_D = +40°$ is dissolved in 5 ml of THF. To the cooled mixture, placed under an inert atmosphere, particularly argon, 1 ml of LiCH$_3$, that is to say 625 μl of a 1.6M solution of methyl lithium is added. After 15 minutes of stirring, 1 mmole of water is added to neutralise the reaction mixture, then the temperature is brought back to 25° C. $^{31}$P NMR analysis (20%.C$_6$D$_6$.THF) indicates the quantitative formation of the aminophoshpine (10) δ $^{31}$P = −26.4 ppm). The structure (10) is confirmed by the formation of a tungsten compound (10') of type (3') with W(CO)$_5$THF by the usual method, that is to say the irradiation of or ½ h of W(CO)$_6$ in THF, after the addition of aminophosphine (10). Purification by chromotography on silica; obtained 410 mg; yield 67%. The characteristics of the complex (10'), not crystallised, follow:

| | | |
|---|---|---|
| δ$^{31}$P = + 64 ppm (CDCl$_3$) | | $J_{PW}$ = 261 Hz |
| $^1$H NMR (CDCl$_3$) | | |
| doublet (3H) | 1,2 ppm | J = 7 Hz |
| doublet (3H) | 1,8 ppm | $J_{PH}$ = 5 Hz |
| doublet (3H) | 2,6 ppm | |
| multiplet (1H) | 3,8 ppm | |
| doublet (1H) | 4,6 ppm | $J_{HH}$ = 8 Hz |
| massif (10H) | 6,8–7,6 ppm | |
| Analysis C$_{22}$H$_{22}$NO$_6$PW | | |
| Calculated: | % C | % H | % N |
| | 43,21 | 3,6 | 2,29 |
| Found: | 43,00 | 3,36 | 2,55 |
| IR (net) | | |
| | $\bar{\nu}_{OH}$ = 3400 cm$^{-1}$ | |
| | $\bar{\nu}_{CO}$ = 2080 cm$^{-1}$, 1926 cm$^{-1}$, 1980 cm$^{-1}$ | |
| Mass: (W = 184) | M$^{.+}$−28 = 583 | |
| rotatory power: | $[\alpha]_D^{19}$ = +7,03 (c = 7.CH$_2$Cl$_2$) | |

The compounds (10) and (10') are novel and illustrate by their example the action of an alkyl lithium according to the reaction scheme (5).

EXAMPLE 2

Preparation of a diastereomer of compound (10) of example 1, namely of N-methyl N-(1-hydroxy 1-phenyl 2propyl) methyl phenyl aminophosphine (R$_p$,1R,2S)

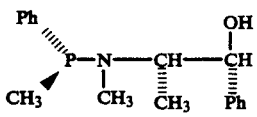

(11)

According to a method similar to that of example 1, 1 mmole of phenyl lithium, that is to say 1 ml of a 1M solution is added to 1 mmole (209 mg) of oxazaphospholidine (5'')

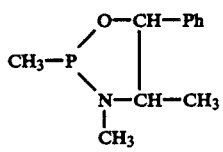

(5'')

After 30 min at −78° C., the reaction mixture is hydrolysed with 40 μl of H$_2$O. $^{31}$P NMR analysis indicates the formation of compound (11): $\delta^{31}$P=−26 ppm, C$_6$D$_6$ +THF. The structure (11) is confirmed by complexation with W(CO)$_5$THF, which leads to compound (11'), a diastereomer of (10'), purified by chromotography on silica (eluant hexane —AcOEt 10%); obtained 310 mg - yield 50%.

Characteristic of compound (11'), that is to say of (11) carrying the complexing group W(CO)$_5$ on the P atom:

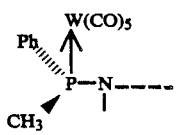

$\delta^{31}$P = +64,1 ppm    J$_{pw}$ = 260 Hz
mass: (W = 184)M$\cdot$± 28 = 583
$^1$H NMR (CDCl$_3$)
doublet (3H)    1,25 ppm    J = 7Hz
doublet (3H)    2,05 ppm    J$_{PH}$ = 5Hz
doublet (3H)    2,55 ppm
multiplet (1H)  3,8 ppm
doublet (1H)    4,6 ppm     J$_{HH}$ = 9Hz
massif (10H)    6,8–7,6 ppm IR(net)  $\bar{v}_{OH}$ = 3400 cm$^{-1}$ $\bar{v}_{C=O}$ = 2080 cm$^{-1}$, 1980 cm$^{-1}$, 1925 cm$^{-1}$ The compounds (11) and (11') are novel and illustrate by way of example the addition of an aryl lithium according to the invention.

EXAMPLE 3

Preparation of N-methyl N-(1-hydroxy 1-phenyl 2-propyl) butyl phenyl aminophosphine (5p, 1R, 2S). According to a method similar to that of example 1, 1 mmole of butyl lithium is added to 271 mg of oxazaphospholidine (5') (R$^1$=Ph). After 2 hours of reaction at a temperature between −78 and −40° C. ($^{31}$P NMR δ=−26.4 ppm), the aminophosphine product was recovered.

EXAMPLE 4

Preparation of a complexed aminophosphine (3') starting with an oxazaphospholidine carrying the complexing group W(CO)$_5$ on the phosphorus

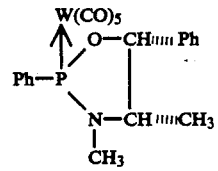

(12)

by the action of CH$_3$Li on the compound (12).

In a 100 ml flask, 595 mg of complex (12) (∼1 mmole) are dissolved in 5 ml of anhydrous THF and placed in an inert atmosphere (Ar) at -78° C. After addition of 1 mmole of methyl lithium, the mixture is left under these conditions for 6 hours, then it is neutralised with 40 μl of water and dried on Na$_2$SO$_4$. The evaporation of solvent gives a residue which is chromatographed on silica (eluant: AcOEt 5%, hexane 95%); obtained 470 mg; yield 77%.

The compound obtained has the same characteristics as the complex (10') prepared according to example 1.

It is to be noted that the compounds are more stable, as well as less subject to oxidation, in their complexed forms.

By analagous operations, but starting from the oxazaphospholidine (5') complexed on P of example 2, and replacing CH$_3$Li by C$_6$H$_5$Li, one obtains the complexed aminophosphine (11') comprising the group

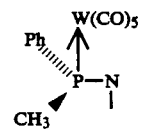

the characteristics of which are given in example 2.

EXAMPLE 5

Preparation of an intermediate product (7) starting from dioxaphosphacycloalkane.

The reaction (5) is applied to a dioxaphosphacycloalkane, that is to say the dioxaphospholane (Q=0)

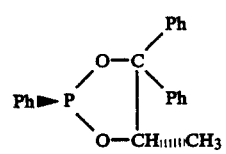

which is reacted with butyl lithium.

In a 100 ml flask, fitted with a stirrer, 334 mg (1 mmole) of dioxaphospholane are dissolved in 5 ml of THF in an atmosphere of argon. To the mixture coiled to −78° C. 1 mmole of butyl lithium, that is 500 μl of 2M solution, is added. After 10 min of stirring the $^{31}$P NMR analysis of the mixture (20% C$_6$D$_6$ of THF) indicates the quantitative formation of phosphinite ( $\delta^{31}$P =−26.5 ppm)

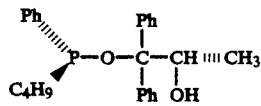

(13)

that is to say, of 1,1-diphenyl, 2-hydroxypropyl butyl phenyl phosphinite (Rp, 2S).

This compound is novel. Its formulation is confirmed by its reaction with the equivalent of CH₃Li at −78° C., directly in the reaction mixture of its preparation, then stopping of the reaction by the addition of H₂O one obtains, with a yield of 61%, the phosphine

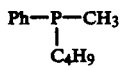

which has the following characteristics.

| $^{31}$P NMR | $\delta = -37$ ppm (20% C₆D₆- THF) |
|---|---|
| $^{1}$H NMR | |
| massif | 0.65–1.78 ppm (9 H) |
| doublet | 1.5 ppm (3 H) $J_{PH} = 15$ Hz |
| massif | 7–7.8 ppm (5 H) |

Example 6

Preparation of a substituted intermediate (7) derived from chloramphenicol, starting from a special dioxaphosphorinane (14).

The compound (14) is the phosphinite (−) 5-dichloroacetamido 4-(4-nitro phenyl) 2-phenyl1,3,2-dioxaphosphrinane (2R,4R,5R)

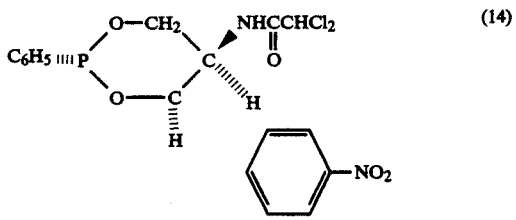

the preparation of which is described in French Patent 2 562 543, on page 8.

The method of the reaction of compound (14) with the o-anisyl lithium

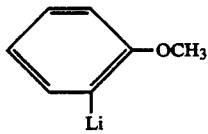

is the same as in example 5, except that three equivalents of o-anisyl lithium, in place of butyl lithium, are added to 429 mg of dioxaphosphorinane (14)

The novel product, obtained after 4 hours at −78→−40° C., is the o-anisyl phenyl phosphinite

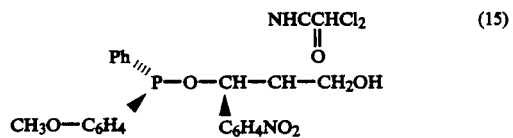

Example 7

Application of complexed intermediate compound (10') in the production of a halogenophosphine (16).

The complex (10'), described in example 1, is treated by gaseous HCl in solution in dichloromethane, to give the reaction:

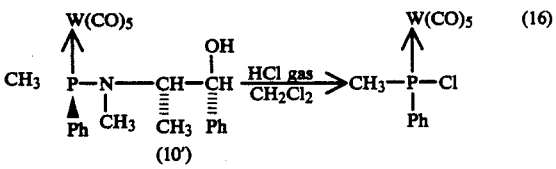

Into a 100 ml flask, 95 mg of complexed aminophosphine (10') dissolved in 10 ml of CH₂Cl₂ were introduced. After bubbling dry HCl gas for 30 min, the CCM indicated the disappearance of starting material. Millipore filtration of the reaction mixture, followed by evaporation of the solvent, gave 70 mg of compound (16) with a yield of 93%. The precipitate, formed in the course of the reaction, turned out to be the chlorohydrate of ephedrine ($[\alpha]_D = -34.6°$).

Characteristics of compound (16):

| $^{31}$PNMR (CDCl₃) | $\delta = 103,6$ ppm | $J_{pw} = 290$ Hz |
|---|---|---|
| $^{1}$H NMR (CDCl₃) | | |
| doublet (3H) | 2,57 ppm | $J_{PH} = 5$ Hz |
| massif (5H) | 7,4–8 ppm | |
| Mass: | (w = 184) | (EI; 70 eV) |
| | M·⁺ = 482 | |
| | | peak of tase 342 (M·⁺ −140) |
| IR (KBr) | | |
| | $\overline{V}_{co} = 2065, 1930$ cm⁻¹ | |

EXAMPLE 8

Application of an intermediate product (10') in the preparation of a phosphinous acid, the complexes being more stable and less oxidisible than the phosphinous compounds themselves, here the complexed compound (10') of example 7 was again used. The decomplexation took place easily, in the known manner, not needing to be described.

The complexed phosphinous acid is obtained by acid hydrolysis starting from the aminophosphine (10')

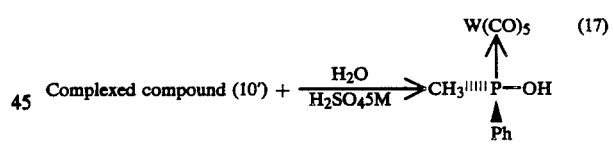

For this, in a 100 ml flask, fitted with an upright condenser, 1 mmole of complexed aminophosphine (611 mg) is heated for 1 hour at 65° C. in 10 ml of a 5M mixture of acetonitrile and sulphuric acid CH₃CH/H₂SO₄ (10:1). After cooling, the mixture is neutralised by NaHCO₃ in saturated acqueous solution, then extracted with CH₂Cl₂. Drying, then evaporation of the organic phase, gives a residue which is chromatographed on silica to separate (AcOET 10% - Hexane - rf 0.4-) the compound (17) obtained 45 mg, yield 97% $[\alpha]_D = +4.80°(c=3\ CH_2Cl_2)$.

| not cristallised | | |
|---|---|---|
| $^{31}$P NMR (CDCl₃) | $\delta = +102,9$ ppm | $J_{pw} = 264$ Hz |
| $^{1}$H NMR | (COCl₃) | |
| doublet (3H) | 2,12 ppm | $J_{PH} = 6$ Hz |
| large singlet (1H) | 4,6 ppm | |
| massif (5H) | 7,3–7,6 ppm | |
| IR: (net) | $\underline{V}_{OH}\ 3600$ cm⁻¹, 2700 cm⁻¹ | |
| | $V_C = O\ 2080$ cm⁻¹, 1925 cm⁻¹ | |
| Mass: | W = 184 (EI, 70eV) | |
| | M'⁺ = 464 | |

EXAMPLE 9

Application of complexed intermediate compound (10') in the preparation of an alkyl phosphinite.

The tungsten complex, the aminophosphine (10') obtained according to example 1, is subjected to the methanolysis which gives:

$$\text{Compound (10')} \xrightarrow{\text{CH}_3\text{OH}}_{\text{H}_2\text{SO}_4 5\text{M}}$$

$$\begin{array}{cc}
\text{W(CO)}_5 & \text{W(CO)}_5 \\
\uparrow & \uparrow \\
\text{CH}_3-\text{P}-\text{OH} & \text{CH}_3-\text{P}-\text{OCH}_3 \\
| & | \\
\text{Ph} & \text{Ph} \\
(17) & (18)
\end{array}$$

In a 100 ml flask, fitted with a stirrer, 560 mg, that is to say 0.92 mol, of complexed aminophosphine (10') are dissolved in 5 ml of 5M methanol/$H_2SO_4$. After 3 hours at ambient temperature, the mixture is neutralised by a saturated solution of $NaHCO_3$ and extracted with $CH_2Cl_2$. Drying and evaporation of the organic phase gives 380 mg of a residue which turned out to be 4:1 mixture of products (17) and (18) (yield 80%), which were separated by chromotography on silica (AcOEt 10% - Hexane).

The rotatory power of the phosphinous ester (18) obtained is $[\alpha]_D = +1.2°(c=1.2\ CH_2Cl_2)$.

In replacing methanol by isopropanol in the above preparation, the homologeous isopropyl ester of product (17) was obtained in two hours at 68° C.

EXAMPLE 10

Application of an intermediate product of the type (7), in particular (13), in the production of a phosphine.

The compound (13) of example (5) is treated by an organometallic compound, particularly by an alkyl or aryl lithium, then the reaction medium is stopped by the addition of a small quantity of water.

1 equivalent of $CH_3Li$ is added to 1 mmole of compound (13) in solution in THF and the mixture is maintained at $-78°$ C. for 10 min. After cold evaporation of solvent, the residue is recovered in hexane and the mineral salts are separated by filtration. A further evaporation gives, with a yield of 61%, 140 mg.

An advantage of the invention is that this operation can be easily carried out in the same reaction medium in which the intermediate compound has been prepared (see example 5).

One can thus carry out in two steps in the same solvent:

$$(1°) - \text{reaction (5)} \longrightarrow \text{compound (7)}$$

$$(2°) - \text{compound (7)} \xrightarrow[\text{H}_2\text{O}]{\text{LiCH}_3} \text{Ph}-\underset{\underset{\text{C}_4\text{H}_9}{|}}{\text{P}}-\text{CH}_3$$

After separation of this latter product, it can be converted into a phosphine oxide, for example by treatment with $H_2O_2$.

EXAMPLE 11

Application of intermediate compound (15) in the preparation of a phosphine.

o-anisyl phenyl phosphinite (15) of example 6 is heated at 60° C. for 3 hours with a stoichiometric quantity of $CH_3I$ in solution in THF. The evaporation of solvent leaves a residue which is chromatographed on silica (acetone).

The product obtained is the oxide of o-anisyl methyl phenyl phosphine $$\text{compound (15)} \xrightarrow{\text{CH}_3\text{I}} \text{CH}_3-\overset{\overset{\text{O}}{\|}}{\underset{\underset{\text{C}_6\text{H}_4-\text{OCH}_3}{\blacktriangle}}{\text{P}}}\ \text{Ph}$$

identified by the following characteristics:

| | $[\alpha]_D^{20} = -11,97°\ (c = 2\ CH_3OH)$ | |
|---|---|---|
| $^1$H NMR | | |
| doublet | 2,05 ppm (3H) | $J_{PH} = 15\ Hz$ |
| singlet | 3,7 ppm (3H) | |
| massif | 6,8–8,1 ppm (3H) | |

As mentioned on above, line 15, $R^1$ can be, in particular, methyl, ethyl, propyl or butyl, $R^2$ being phenyl or vice-versa.

EXAMPLE 12

Preparation of N-methyl N-(1-hydroxy 1-phenyl 2-propyl) o-anisyl phenyl phosphine ($R_p$; 1R, 2S)

$$\begin{array}{c}
\text{OCH}_3 \\
\diagdown\diagup \\
\langle\bigcirc\rangle\text{\tiny{IIIIIIII}}\text{P}-\text{N}-\overset{\text{OH}}{\underset{|}{\text{CH}}}-\text{CH} \\
\overset{\blacktriangleleft}{\text{Ph}}\ \ \ |\ \ \ \ \ \ \ |\ \ \ \ \ \ |\\
\ \ \ \ \ \ \ \text{CH}_3\ \ \text{CH}_3\ \text{Ph}
\end{array} \quad (19)$$

This is the compound of formula (3) given above, in which $R^1$ is o-anisyl, $R^2$ and $R^5$ phenyls, $R^3$ and $R^4$ methyls, $R^6$ and $R^7$ hydrogen atoms, while T is only a simple bond. The compound 19 is novel. The preparation is carried out according to a method similar to that of example 1, by replacing methyl lithium by o-anisyl lithium. The duration of reaction is then 3 hours, and the temperature increased gradually from $-78$ to $-20°$ C. The aminophosphine is not isolated, but trapped with two equivalents of methyl iodide to give the oxide of o-anisyl methyl phenyl phosphine described in example 11. Here the reaction is $$\begin{array}{c}
\text{OCH}_3\ \ \ \ \ \ \ \ \ \ \text{O}^\ominus \\
\ \ \ \ \ \ \ \ \ \ \ \ \ \ \ \ \ \ | \\
\ \ \ \ \ \ \ \ \ \ \ \ \ \ \ \ \text{CH}\text{\tiny{IIII}}\text{Ph} \\
\langle\bigcirc\rangle\text{\tiny{IIIIIIII}}\text{P}-\text{N}-\text{CH}\ \ \ \ +\ \text{CH}_3\ \text{I} \longrightarrow \\
\overset{\blacktriangleleft}{\text{Ph}}\ \ \ |\ \ \ \ \ \ |\ \\
\ \ \ \ \ \ \text{CH}_3\ \ \text{CH}_3
\end{array}$$

$$\begin{array}{c}
\text{OCH}_3 \\
\ \ \ \ \ \ \ \ \ \ \ \ \ \ \ \text{CH}_3 \\
\ \ \ \ \ \ \ \ \ \ \ \ \ \ \ | \\
\langle\bigcirc\rangle\text{\tiny{IIIIIIII}}\text{P}_\oplus-\text{N}-\text{O}^\ominus \longrightarrow \\
\overset{\blacktriangleleft}{\text{Ph}}\ \ \ \ \ \ \ \ \ | \\
\ \ \ \ \ \ \ \ \ \ \ \ \ \ \text{CH}_3
\end{array}$$

-continued

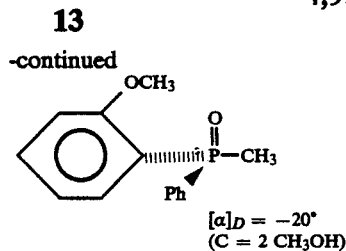

$[\alpha]_D = -20°$
(C = 2 CH$_3$OH)

EXAMPLE 13

Preparation of a phosphinite intermediate product (7) starting from a dioxaphosphacycloalkane obtained by condensation of (2-methoxy phenyl) dichloro phosphine with the (−) 1,1-diphenyl propan-1,2-diol (2S) (20)

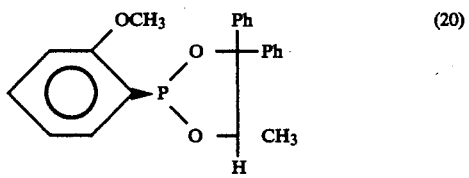
(20)

which is a new compound. According to the method described in example 5, 1 mmol of dioxaphospholane (20) is reacted with 1 equivalent of methyl lithium in 10 ml of THF at −78° C. After 5 mins of stirring, $^{31}$P NMR analysis indicates $\delta^{31}P = 26$ ppm which is characteristic of phosphinite (21)

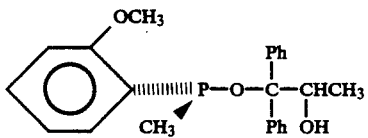
(21)

The 1,1-diphenyl, 2-hydroxy propyl o-anisyl methyl phosphinite (R$_p$, 2S) is a new compound. Its formation is confirmed by the addition of an equivalent of phenyl lithium. After half an hour, the mixture is hydrolysed and evaporated to dryness (weight obtained 33 mg). $^1$H NMR analysis indicates a mixture of o-anisyl methyl phenyl phosphine and some 1,1-diphenyl propan-1,2-diol. Yield of phosphine: 50%.

| Clear yellow oil | | | | |
|---|---|---|---|---|
| $^1$H NMR o-anisyl methyl phenyl phosphine (CDCl$_3$) | | | | |
| doublet | (3H) | $J_{HP}$ 4 Hz | | 1.63 ppm |
| singlet | (3H) | | | 3.85 ppm |
| massif | (9H) | | | 7.79 ppm |

The addition of 5 ml of 20% H$_2$O$_2$ to the medium effected the transformation to phosphine oxide. After washing with water and extraction with dichloromethane, the organic phase is evaporated and the residue is chromatographed on silica (eluant acetone —rf 0.5). The phosphine oxide is obtained with a yield of 50%. $[\alpha]_D = -5.1°$(20 ee)

EXAMPLE 14

Application of the complexed phosphinous acid complex (17) is the preparation of methyl phosphinite (18).

The tungsten complex (17) ([$\alpha$]$_D$=17°pF=115°) was obtained according to the method described in example 9 (5M isopropanol/H$_2$SO$_4$). 100 mg of complex (17) was disolved in 10 ml of an ether solution of diazomethane 0.4 M at 0° C. After four hours of stirring, the solution is evaporated and chromatographed on silica: 10% AcOEt/Hexane (rf 0.8). The phosphinite (18) is obtained with a 60% yield (63 mg).

| $[\alpha]_D = +1.46°$ (c = CH$_2$Cl$_2$) | | |
|---|---|---|
| $^1$H NMR (CDCl$_3$) | | |
| doublet (3H) | 2.15 ppm | $J_{PH} = 6$ H$_z$ |
| doublet (3H) | 3.5 ppm | $J_{POCH} = 12$ H$_z$ |
| massif (5H) | 7.5-7.8 ppm | |
| $^{31}$P NMR (CDCl$_3$) = +114 ppm | | |

EXAMPLE 15

Preparation of a phosphinite intermediate (23) complexed to a W(CO)$_5$ group

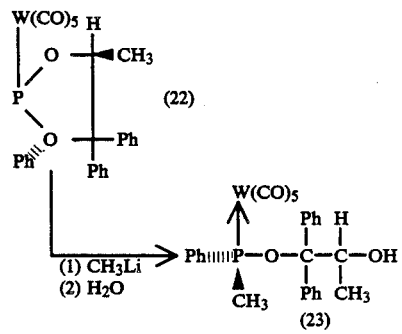

The complexed phosphinite (23) corresponds to the formula (7) in which R$^1$, R$^4$ and R$^6$ are phenyls, R$^2$ and R$^5$ methyls, R$^7$ a hydrogen and T a bond. The atom of phosphorus is held in the coordination sphere of tungsten (W(CO)$_5$). This novel compound is obtained by the action of methyl lithium on the phosphonite complex (22) (−78° C.; THF; 2 h; yield 60%). The product (23) is purified by chromatography on silica (15% AcOEt/Hexane:rf:0.3).

| Oil | | |
|---|---|---|
| $^1$H NMR (CDCl$_3$) | | |
| doublet (3H) | 1.15 ppm | JHH = 7 Hz |
| doublet (3H) | 2 ppm | $J_{PH} = 4$ Hz |
| multiplet (1H) | 5.1 ppm | |
| singlet (1H) | 2.9 ppm | |
| massif (15H) | 7-7.8 ppm | |
| $[\alpha]_D = 11°$ (C = 2 CHCl$_3$) | | |

The precursor complex (22) is a novel compound prepared according to a conventional method, that is to say irradiation ½h of W(CO)$_6$ in THF, then addition of dioxaphospholane obtained by reaction of dichlorophenylphosphine with the (−) 1,1-diphenyl propan-1,2-diol. The purification of this complex (22) is carried out by chromatography on silica (eluant: 10% AcOEt/Hexane - rf 0.6).

| PF = 150° C. | | |
|---|---|---|
| $[\alpha]_D = -85°$ (C = 3.6 CHCl$_3$) | | |
| $^1$H NMR (CDCl$_3$) | | |
| doublet (3H) | 1.15 ppm | J = 8 Hz |
| double quadruplet | 4.85 ppm | $J_{HH} = 8$ Hz (1H) |
| massif (15H) | 7-7.8 ppm | $J_{POCH} = 2$ Hz |

We claim:

1. A phosphine of the formula

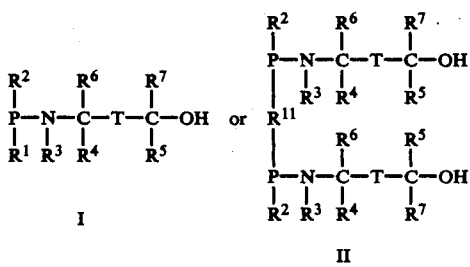

I in which the groups $R^1$ to $R^7$ are individually selected from the group consisting of hydrogen and 1 to 18 carbon atom alkyl, alkenyl, cycloalkyl and phenyl groups, T is alkylene, arylene or a bond and $R^{11}$ is a 1 to 18 carbon alkylene, alkenylene, cycloalkylene or phenylene group.

2. The phosphine of claim 1, in which T is a bond and the organic groups represented by $R^1$ to $R^7$ and $R^{11}$ contain 1 to 6 carbon atoms.

3. A phosphine according to claim 2, in which $R^1$ to $R^7$ are individually selected from the group consisting of hydrogen, alkyl, alkenyl and phenyl groups, and $R^{11}$ is alkylene, alkenylene or phenylene.

4. The phosphine of claim 3 having formula II.

5. A phosphine according to claim 3 of formula I, in which $R^1$, $R^3$, and $R^4$ are methyl, $R^6$ and $R^7$ are hydrogen and $R^2$ and $R^5$ are phenyl, said phosphine being optically active.

6. A phosphine according to claim 3 of formula I, in which one of $R^1$ and $R^2$ is methyl and the other of $R^1$ and $R^2$ is phenyl.

7. A phosphine according to claim 3 of formula I, in which $R^1$ and $R^5$ are phenyl, $R^2$ is ortho-anisyl, $R^3$ and $R^4$ are methyl, and $R^6$ and $R^7$ are hydrogen, said phosphine being optically active.

8. A phosphine according to claim 3, in which one of $R^1$ and $R^2$ is methyl, ethyl, propyl or butyl and the other is phenyl and in which one member of the moieties $R^3$ through $R^7$ is methyl and a second member of the group is phenyl, said phosphine being optically active.

9. A phosphine according to claim 1 of formula I, in which T is $NHCOCHCl_2$ substituted methylene, $R^4$ is nitrophenyl, and $R^5$, $R^6$ and $R^7$ are hydrogen.

10. A process for the preparation of the phosphine of claim 1, comprising reacting an organometallic compound $R^2M$ with a phosphacycloalkane of the formula

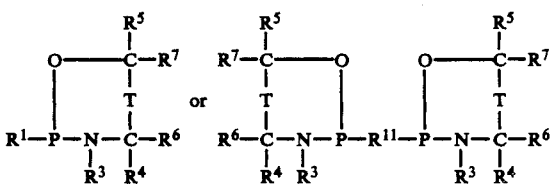

in which the symbols $R^1$ through $R^7$, $R^{11}$ and T have the same meaning as set forth in claim 1 and in which M is at least one metal selected from the group consisting of Mg, Al, Zn and Li, and thereafter hydrolyzing the reaction product thus obtained.

11. A method according to claim 10, in which the reaction between the organometallic compound and the phosphacycloalkane is carried out at a temperature between $-78$ and $-48°$ C.

12. A method according to claim 10, in which M is lithium and $R^2$ is $C_{1-4}$ alkyl, phenyl or anisyl.

* * * * *